United States Patent [19]

Strike

[11] 4,059,701
[45] Nov. 22, 1977

[54] 15-SUBSTITUTED PROSTANOIC ACIDS FOR TREATING BRONCHIAL SPASM

[75] Inventor: Donald Peter Strike, St. Davids, Pa.

[73] Assignee: American Home Products Corporation, New York, N.Y.

[21] Appl. No.: 678,085

[22] Filed: Apr. 19, 1976

Related U.S. Application Data

[60] Division of Ser. No. 569,026, April 17, 1975, Pat. No. 4,022,821, which is a division of Ser. No. 462,006, April 18, 1974, abandoned, which is a continuation-in-part of Ser. No. 383,007, July 26, 1973, Pat. No. 3,922,302.

[51] Int. Cl.$^2$ ............... A61K 31/495; A61K 31/215; A61K 31/19
[52] U.S. Cl. .................................. 424/250; 424/267; 424/274; 424/305; 424/317
[58] Field of Search ............... 424/267, 250, 274, 305, 424/317

[56] References Cited

U.S. PATENT DOCUMENTS

| | | | |
|---|---|---|---|
| 3,773,795 | 11/1973 | Bagli et al. | 260/345.7 |
| 3,816,393 | 6/1974 | Hayashi et al. | 260/209 R |

*Primary Examiner*—Sam Rosen

*Attorney, Agent, or Firm*—David E. Frankhouser

[57] ABSTRACT

There is disclosed herein a process for relieving bronchial spasm and facilitating breathing in warm-blooded animals which comprises administering to a warm-blooded animal in need thereof an amount sufficient to relieve bronchial spasm and facilitate breathing in said warm-blooded animal of a prostanoic acid of the formula:

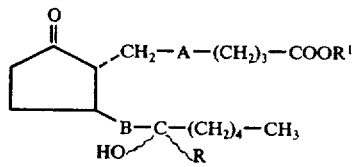

wherein R is ethynyl, A is —CH$_2$—CH$_2$— and B is —CH$_2$—CH$_2$—; R is ethynyl, A is —CH$_2$—CH$_2$—, and B is trans —CH=CH—; or R is ethynyl, A is cis —CH=CH—; and B is trans —CH=CH—; and R$^1$ is hydrogen, alkyl of from 1 to about 6 carbon atoms, alkali metal, or a pharmacologically acceptable cation derived from ammonia or a basic amine.

2 Claims, 3 Drawing Figures

15-SUBSTITUTED PROSTANOIC ACIDS FOR TREATING BRONCHIAL SPASM

CROSS-REFERENCE TO COPENDING APPLICATION

This application is a division of copending application Ser. No. 569,026, filed Apr. 17, 1975, now U.S. Pat. No. 4,022,821 which is a division of application Ser. No. 462,006, filed Apr. 18, 1974, now abandoned, which is a continuation-in-part of application Ser. No. 383,007, filed July 26, 1973, now U.S. Pat. No. 3,922,302.

BACKGROUND OF THE INVENTION

The prostaglandins are a group of hormone-like substances which may be viewed as derivatives of prostanoic acid. Several prostaglandins are found widely distributed in mammalian tissue and have been isolated from this source. These prostaglandins have been shown to possess a variety of biological properties such as bronchodilation, the ability to reduce gastric secretion, to modify muscle tone, as well as the ability to raise or lower blood pressure.

Various derivatives of prostaglandins have also been synthesized and reported. 9,15-Dihydroxy prost-13-enoic acid and methods of synthesis thereof are disclosed in U.S. Pat. Nos. 3,432,541 and 3,455,992. 9-Oxo-15-hydroxy-15-methyl-prostanoic acid, 15-oxo-9-hydroxy-prostanoic acid, and 9,15-dioxo prostanoic acid are disclosed in U.S. Pat. No. 3,671,570.

The present invention concerns a number of new intermediates useful in the synthesis of 9-oxo-15-hydroxy-15-methylprostanoic acid as well as new unsaturated 15-methyl derivatives which are themselves useful. In addition 9-oxo-15-hydroxy-15-ethynyl prostanoic acids and new intermediates thereto are included.

SUMMARY OF THE INVENTION

The invention sought to be patented in a first composition aspect resides in the concept of a chemical compound which is prostanoic acid of the structure:

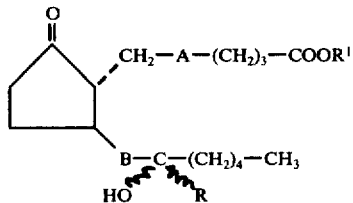

I wherein R is methyl, A is cis—CH=CH— and B is trans—CH=CH—; R is ethynyl, A is —CH$_2$—CH$_2$— and B is CH$_2$—CH$_2$—; R is ethynyl, A is —CH$_2$—CH$_2$— and B is trans—CH=CH—; or R is ethynyl, A is cis—CH=CH— and B is trans—CH=CH—; and R$^1$ is hydrogen, alkyl of from 1 to about 6 carbon atoms, alkali metal, or a pharmacologically acceptable cation derived from ammonia or a basic amine.

The tangible embodiments of the first composition aspect of the invention possess the inherent general physical properties of being clear to yellow oils, or crystalline solids, and when R$^1$ is hydrogen are substantially insoluble in water and are generally soluble in organic solvents such as ethyl acetate and ether. Examination of the compounds produced according to the hereinafter described process reveals, upon infrared, nuclear magnetic resonance, and mass spectrographic analysis, spectral date supporting the molecular structures herein set forth. The aforementioned physical characteristics, taken together with the nature of the starting materials, the mode of synthesis, and the elemental analyses, confirm the structure of the compositions sought to be patented.

The tangible embodiments of the first composition aspect of the invention possess the inherent applied use characteristic of exerting bronchodilating effects upon administration to warm-blooded animals as evidenced by pharmacological evaluation according to standard test procedures.

The invention sought to be patented in a second composition aspect resides in the concept of a chemical compound which is a prostanoic acid of the structure:

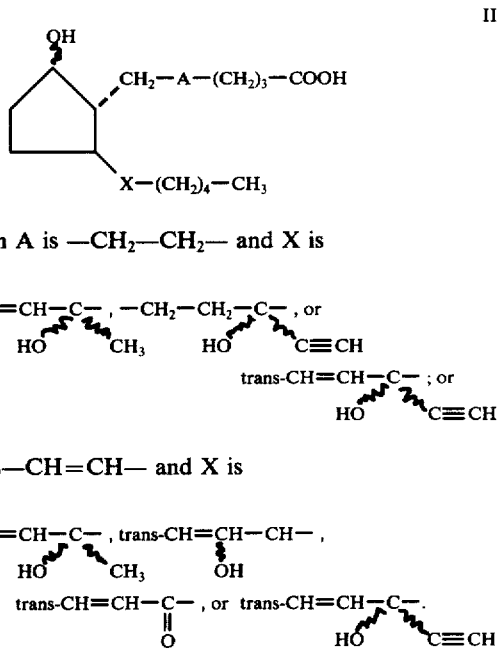

II wherein A is —CH$_2$—CH$_2$— and X is

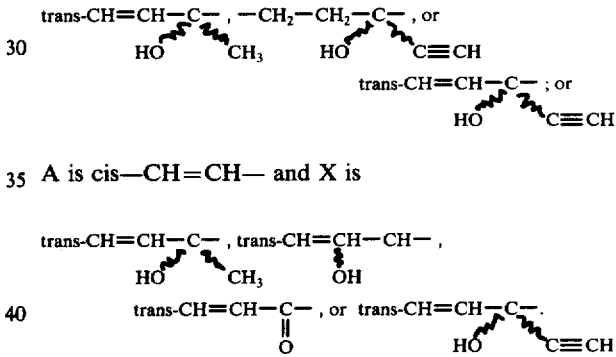

A is cis—CH=CH— and X is trans-CH=CH—C— , trans-CH=CH—CH— ,
HO' 'CH$_3$      OH trans-CH=CH—C— , or trans-CH=CH—C—.
       ‖                    HO' 'C≡CH
       O The tangible embodiments of the second composition aspect of the invention possess the inherent general physical properties of being clear to yellow oils, are substantially insoluble in water and are generally soluble in organic solvents such as ethyl acetate and ether.

Examination of the compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, the mode of synthesis, and the elemental analyses, confirm the structure of the compositions sought to be patented.

The embodiments of the second composition aspect of the invention possess the inherent applied use characteristics of being useful as intermediates for the synthesis of other compositions of the invention having bronchodilating activity, and, in addition, those compounds having a cis-5-en, a trans-13-ene, a 9-hydroxy group and having in the 15-position either a keto group or a hydrogen and hydroxy substituent, or those having hydroxy and methyl substituents at the 15-position are intermediates for the synthesis of 9-oxo-15-hydroxy-15-methyl-prostanoic acid.

The invention sought to be patented in its process aspect resides in the concept of a method of relieving bronchial spasm and facilitating breathing in warm-blooded animals which comprises administering to a warm-blooded animal in need thereof an amount sufficient to relieve bronchial spasm and facilitate breathing in said warm-blooded animal of a prostanoic acid of the formula:

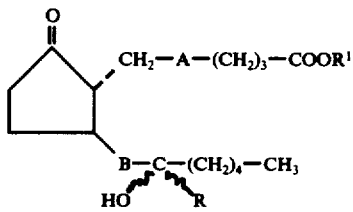

wherein R is methyl, A is a cis—CH=CH— and B is trans—CH=CH—; R is ethynyl, A is —CH$_2$—CH$_2$— and B is —CH$_2$—CH$_2$—; R is ethynyl, A is —CH$_2$—CH$_2$— and B is trans—CH=CH—; or R is ethynyl, A is cis—CH=CH— and B is trans—CH=CH—; and R$^1$ is hydrogen, alkyl of from 1 to about 6 carbon atoms, alkali metal, or a pharmacologically acceptable cation derived from ammonia or a basic amine.

The invention sought to be patented in a third composition aspect resides in the concept of a chemical compound which is a prostanoic acid of the structure

XXIII

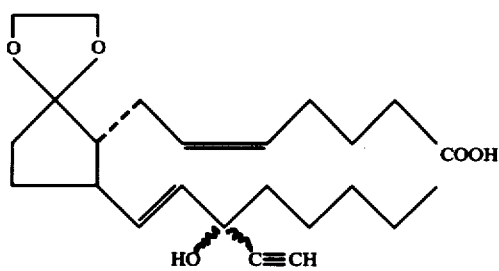

The tangible embodiments of the third composition aspect of the invention possess the inherent general physical properties of being clear to yellow oils, are substantially insoluble in water, and are soluble in organic solvents such as ethylacetate and ether.

Examination of the compounds produced according to the hereinafter described process reveals, upon infrared, nuclear magnetic resonance and mass spectrographic analysis, spectral data supporting the molecular structure herein set forth. The aforementioned physical characteristics, taken together with the mode of synthesis, and the elevated analyses, confirm the structure of the compositions sought to be patented. The embodiments of the third composition aspect of the invention possess the inherent applied use characteristic of being intermediates in the synthesis of compounds of Formula I wherein R is ethynyl, A is cis—CH=CH—, and B is trans—CH=CH—.

DESCRIPTION OF THE PREFERRED EMBODIMENTS

In describing the synthesis of the compositions of the invention reference will be made to FIGS. 1, 2, and 3 wherein the formulae representing the various embodiments of the invention have been assigned Roman numerals for purposes of identification.

Figure 1:
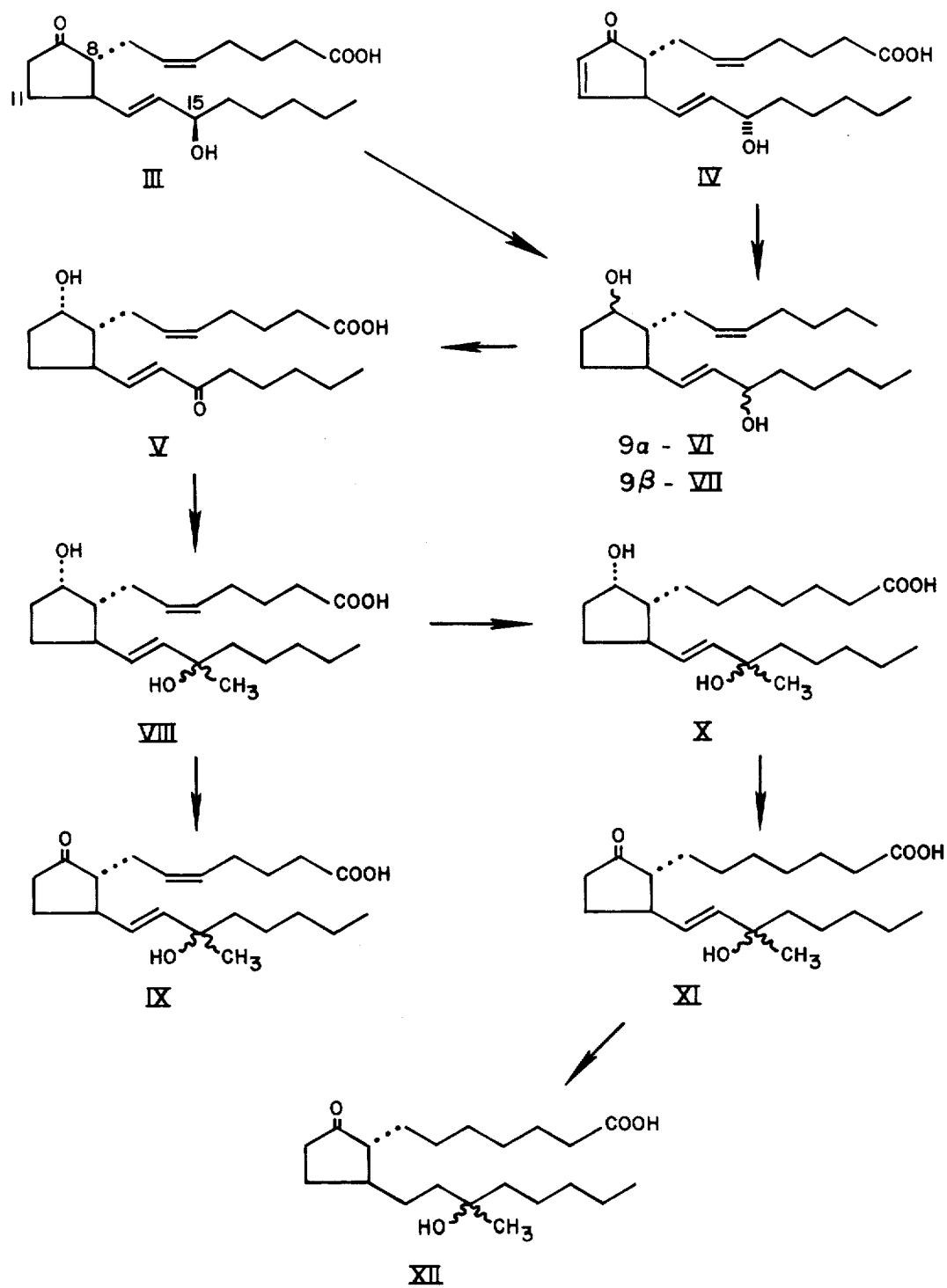

FIG. 1 illustrates the synthesis of a specific embodiment of Formula I namely: 7-(2β-[(3RS)-3-hydroxy-3-methyl-trans-1-octenyl]-5-oxo-1α-cyclopentyl)-cis-5-heptenoic acid (IX) and the synthesis of specific embodiments of Formula II namely: 7-(5α-hydroxy-2β-[(3R)-3-hydroxy-trans-1-octenyl]-1α-cyclopentyl)-cis-5-heptenoic acid (VI); 7-(5β-hydroxy-2β-[(3R)-3-hydroxy-trans-1-octenyl]-1α-cyclopentyl)-cis-5-heptenoic acid (VII); 7-(5α-hydroxy-2β-[3-oxo-trans-1-octenyl]-1α-cyclopentyl)-cis-5-heptenoic acid (V); 7-(5α-hydroxy-2β-[(3RS)3-hydroxy-3-methyl-trans-1-octenyl]-1α-cyclopentyl)-cis-5-heptenoic acid (VIII); 5α-hydroxy-2β-[(3RS)-3-hydroxy-3-methyl-trans-1-octenyl]-1α-cyclopentane-heptanoic acid (X); and the synthesis of the known compound 2β-[(3RS)-3-hydroxy-3-methyloctyl]-5-oxo-1α-cyclopentaneheptanoic acid (XII).

Figure 2:
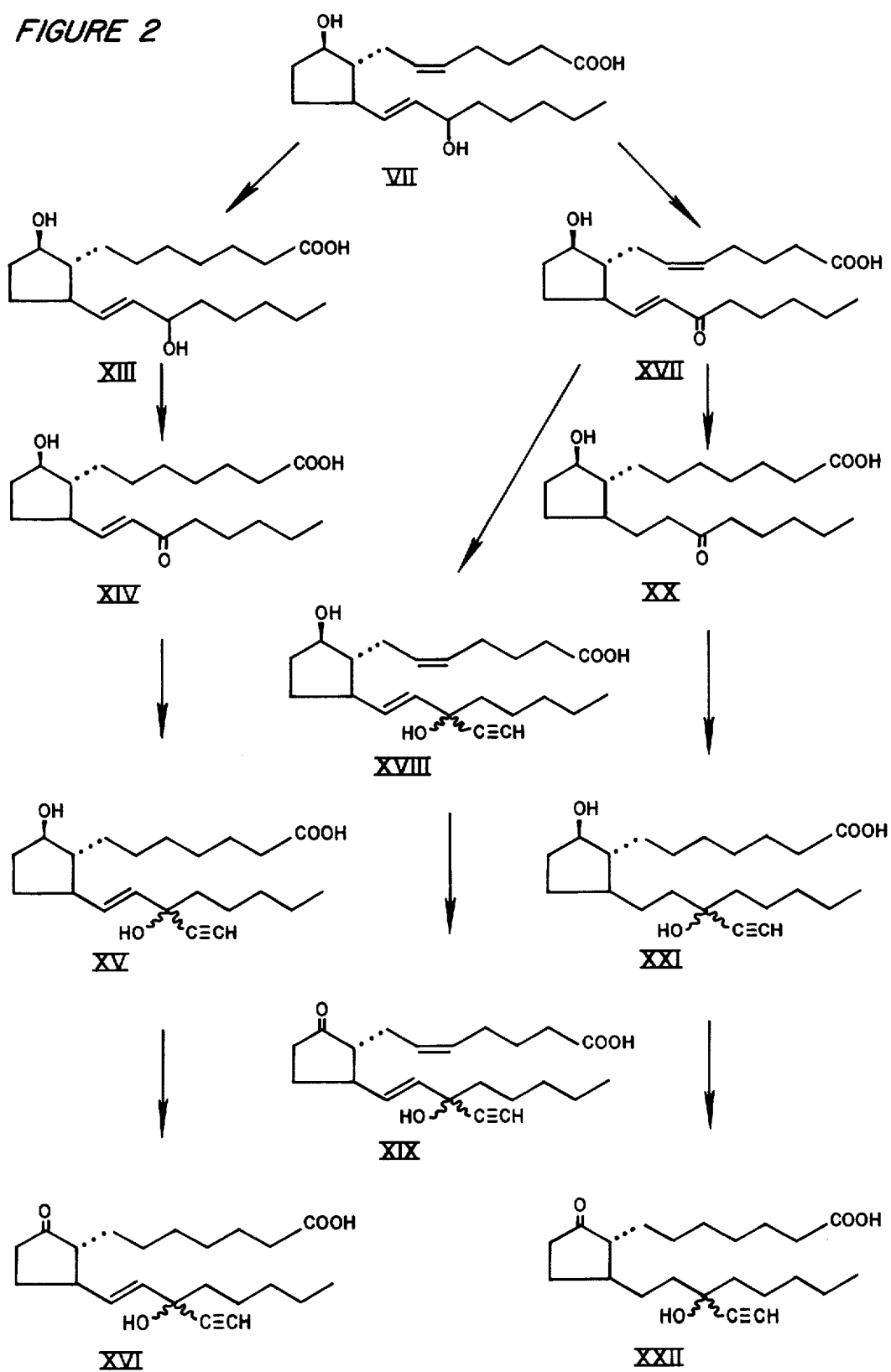

FIG. 2 illustrates the synthesis of other embodiments of Formula I namely 2β-[(3RS)-3-ethynyl-3-hydroxy-trans-1-octenyl]-5-oxo-1α-cyclopentane heptanoic acid (XVI); 2β-[(3RS)-3-ethynyl-3-hydroxy-octyl]-5-oxo-1α-cyclopentane heptanoic acid (XXII); and 7-(2β-ethynyl-3-hydroxy-trans-1-octenyl]-5-oxo-1α-cyclopentyl)-cis-5-heptenoic acids (XIX); and of other embodiments of Formula II namely: 7-(5β-hydroxy-2β-[3-oxo-trans-1-octenyl]-1α-cyclopenty-l0-cis-5-heptenoic acid (XVII); 2β-[(3RS)-3-ethynyl-3-hydroxy octyl]-5β-hydroxy-1α-cyclopentane heptanoic acid (XXI); 2β-[(3RS)-3-ethynyl-3-hydroxy-trans-1-octenyl]-5β-hydroxy-1α-cyclopentane heptanoic acid (XV) and 7-(2β-[(5RS)-3-ethynyl-3-hydroxy-trans-1-octenyl]-5β-hydroxy-1α-cyclopentyl)-cis-5-heptenoic acid (XVIII).

Figure 3:
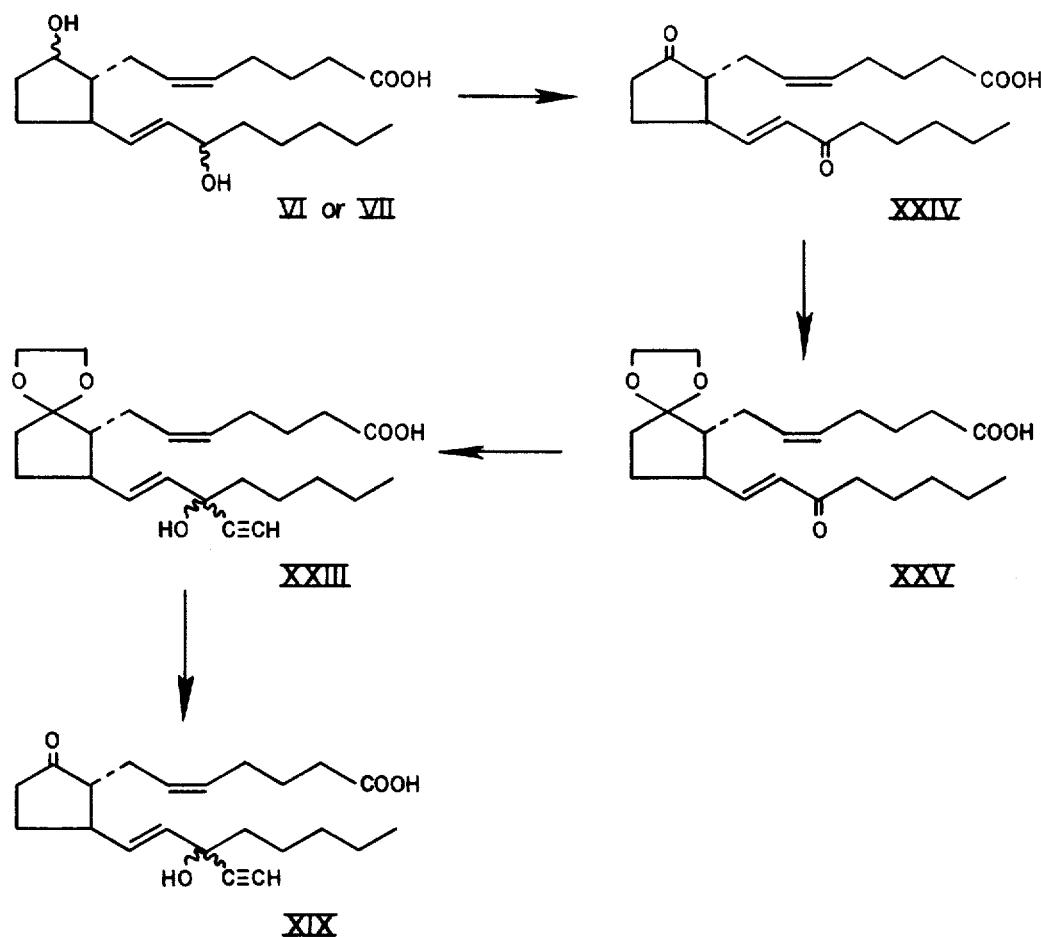

FIG. 3 illustrates an alternative synthesis of XIX utilizing the embodiments of Formula XXIII, namely 7-(7β-[(3RS)-3-ethynyl-3-hydroxy-trans-1-octenyl]-1,4-dioxaspiro[4,4]non-6α-yl)-cis-5-heptenoic acid (XXIII).

The starting materials in the synthesis of the compositions of the invention, namely 15-epi PGA$_2$ (III), and PGA$_2$ (IV) are well-known in the art. For example, 15-epi PGA$_2$ may be obtained from the coral *Plexaura homomalla* by a procedure as described by A. Weinheimer and R. Spraggins in Tetrahedron Letters, 59, 5185 (1969), and PGA$_2$ may, if desired, be prepared from 15-epi PGA$_2$ by an epimerization procedure as described by Bundy et al. in Annals of the New York Academy of Sciences, 180, 76, (April 30, 1971). Sodium borohydride reduction of either III or IV yields a mixture of compounds VI and VII wherein the hydroxyl group at the C-15 position will have an orientation corresponding to that of the starting material selected. Compounds VI and VII may, if desired, be separated by chromatography. Oxidation of VI with dichlorodicyanoquinone (DDQ) gives the enone V. Treatment of V with methyl magnesium bromide gives VIII which may be converted to IX by a Jones oxidation, or hydrogenated using tris(triphenylphosphine)rhodium (I) chloride to give X. Jones oxidation of X gives XI which may be hydrogenated using a palladium on charcoal catalyst to give XII.

If desired, compounds VII may be monohydrogenated using tris-(triphenyl-phosphine)-rhodium (i) chloride to give compound XIII. Oxidation of XIII using DDQ gives XIV. Reaction of XIV and ethynyl magnesium bromide gives XV. Jones oxidation of XV gives compound XVI.

DDQ oxidation of compound VII gives compound XVII. Reaction of XVII with ethynyl magnesium bromide gives XVIII which is converted, if desired, to XIX. Upon chromatography of XIX two products are isolated which are C-15 isomers, and which exhibit identical infrared, nuclear magnetic resonance, and mass spectra.

Hydrogenation of XVII using a palladium on charcoal catalyst gives compound XX which when treated with ethynyl magnesium bromide is converted to XXI. Jones oxidation of XXI gives XXII.

It will be obvious to one skilled in the art that compound VII or mixtures of compounds VI and VII may be substituted for compound VI as starting intermediate in the synthesis of IX and XII and that the intermediates thereto which correspond to V, VIII, and X will have the ring-hydroxyl group in a spatial orientation corresponding to that of the starting intermediate selected.

Similarly compound VI or mixtures of compound VI and VII may be substituted for compound VII as starting intermediate in the synthesis of XVI, XIX, and XXII, and the intermediates thereto namely those corresponding to XIII, XIV, XV, XVII, XVIII, XX, and XXI will similarly have the ring-hydroxyl group in a spatial orientation corresponding to that of the starting intermediate selected.

Jones oxidation of compound VI or VII or mixtures thereof gives 7-[2β-(3-oxo-trans-1-octenyl)-5-oxo-1α-cyclopentyl]-cis-5-heptenoic acid (XXIV). If desired, XXIV may be isolated by standard techniques. Chromatography on silica gel is a convenient method. Treatment of XXIV with ethylene glycol in the presence of an acid catalyst and inert solvent, while removing the water formed gives 7-(7β-[3-oxo-trans-1-ocetnyl]-1,4-dioxaspiro[4,4]non-6α-yl)cis-5-heptenoic acid (XXV). If desired, XXV may be isolated by standard techniques. Chromatography on silica gel is a convenient method. Ethynylation of XXV gives XXIII. XXIII may, if desired, be separated by standard techniques. Chromatography on silica gel is a convenient method and enables the separation of C-15 isomers, which are formed by the synthesis reaction. Treatment of XXIII with aqueous acid gives XIX. The orientation of the C-15 isomer of XIX so obtained will correspond to that of XXIII used. If desired, XIX may be isolated by standard techniques. Chromatography on silica gel is a convenient method.

It will be apparent to those skilled in the art of chemistry that the carbon atoms on the octane side chain to which hydroxyl substituents are attached are assymetric carbon atoms, and as a consequence these positions can be either of two epimeric configurations. The symbol ⩗ where used in this specification is to indicate that both possible configurations at each particular position is intended and is included within the scope of the invention.

The esters of formula I (R¹ is alkyl) are prepared by standard methods, such as for example, by treating a solution of the free acids with diazomethane or other appropriate diazohydrocarbons, such as diazoethane, 1-diazo-2-ethylpentane, and the like. The alkali metal carboxylates of the invention can be prepared by mixing stoichiometrically equivalent amounts of the free acids of formula I, preferably in aqueous solution, with solutions of alkali metal bases, such as sodium, potassium, and lithium hydroxides or carbonates, and the like, then freeze drying the mixture to leave the product as a residue. The amine salts can be prepared by mixing the free acids, preferably in solution, with a solution of the appropriate amine, in water, isopropanol, or the like, and freeze drying the mixture to leave the product as a residue.

The term "alkyl of from about 1 to about 6 carbon atoms" when used herein and in the appended claims includes straight and branched chain hydrocarbon radicals, illustrative members of which are methyl, ethyl, n-propyl, i-propyl, n-butyl, t-butyl, n-pentyl, n-hexyl, 3-methylpentyl, 2,3-dimethylbutyl, and the like. "Alkali metal" includes, for example, sodium, potassium, lithium, and the like. A "pharmacologically-acceptable cation derived from ammonia or a basic amine" contemplates the positively charged ammonium ion and analogous ions derived from organic nitrogenous bases strong enough to form such cations. Bases useful for the purpose of forming pharmacologically-acceptable non-toxic addition salts of such compounds containing free carboxyl groups form a class whose limits are readily understood by those skilled in the art. Merely for illustration, they can be said to comprise, in cationic form, those of the formula:

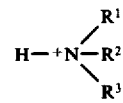

wherein R¹, R², and R³, independently, are hydrogen, alkyl of from about 1 to about 6 carbon atoms, cycloalkyl of from about 3 to about 6 carbon atoms, monocarbocyclicaryl of about 6 carbon atoms, monocarbocyclicarylalkyl of from about 7 to about 11 carbon atoms, hydroxyalkyl of from about 1 to about 3 carbon atoms, or monocarbocyclicarylhydroxyalkyl of from about 7 to about 15 carbon atoms, or, when taken together with the nitrogen atom to which they are attached, any two of R¹, R², and R³ form part of a 5 to 6-membered heterocyclic ring containing carbon, hydrogen, oxygen, or nitrogen, said heterocyclic rings and said monocarbocyclicaryl groups being unsubstituted or mono- or dialkyl substituted, said alkyl groups containing from about 1 to about 6 carbon atoms. Illustrative therefore of R groups comprising pharmacologically-acceptable cations derived from ammonia or a basic amine are ammonium, mono-, di-, and trimmethylammonium, mono-, di- and triethylammonium, mono-, di-, and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butylpiperidinium, 2-methylpiperidinium, 1-ethyl-2-methylpiperidinium, mono-, di- and triethanolammonium, ethylidiethanolammonium, n-butylmonoethanolammonium, tris(hydroxymethyl)-methylammonium, phenylmonoethanolammonium, and the like.

In practicing the method of the invention, the instant compositions can be administered in a variety of dosage forms, the oral route being used primarily for maintenance therapy while injectables tend to be more useful in acute emergency situations. Inhalation (aerosols and solution for nebulizers) seems to be somewhat faster acting than other oral forms but slower than injectables and this method combines the advantages of maintenance and moderately-acute stage therapy in one dosage unit.

The daily dose requirements vary with the particular compositions being employed, the severity of the symptoms being presented, and the animal being treated. The dosage varies with the size of the animal. With large animals (about 70 kg. body weight), by the oral inhalation route, with for example a hand nebulizer or a pressurized aerosol dispenser the dose is from about 5 micrograms to about 100 micrograms, and preferably from about 10 to about 50 micrograms, approximately every four hours, or as needed. By theoral ingestion route, the effective dose is from about 1 to about 20 mg., preferably from about 5 to about 15 mg. up to a total of about 40 mg. per day. By the intravenous route, the ordinarily effective dose is from about 50 micrograms to about 300 micrograms, preferably about 200 micrograms per day.

For unit dosages, the active ingredient can be compounded into any of the usual oral dosage forms including tablets, capsules and liquid preparations such as elixirs and suspensions containing various coloring, flavoring, stabilizing and flavor masking substances. For compounding oral dosage forms the active ingredient can be diluted with various tableting materials such as starches of various types, calcium carbonate, lactose, sucrose and dicalcium phosphate to simplify the tableting and capsulating process. A minor proportion of magnesium stearate is useful as a lubricant. In all cases, of course, the proportion of the active ingredient in said composition will be sufficient to impart bronchodilating activity thereto. This will range upward from about 0.0001% by weight of active ingredient in said composition.

For administration by the oral inhalation route with conventional nebulizers or by oxygen aerosolization it is convenient to provide the instant active ingredient in dilute aqueous solution, preferably at concentrations of about 1 part of medicament to from about 100 to 200 parts by weight of total solution. Entirely conventional additives may be employed to stabilize these solutions or to provide isotonic media, for example, sodium chloride, sodium citrate, citric acid, sodium bisulfite, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispersing agent such as oleyl alcohol. Suitable means to employ the aerosol inhalation therapy technique are described fully in U.S. Pat. Nos. 2,868,691 and 3,095,355, for example.

The following examples further illustrate the best mode contemplated by the inventor of making the compositions of the invention.

EXAMPLE 1

7-(5α-Hydroxy-2β-[(3R)-3-Hydroxy-Trans-1-Octenyl]-1α-Cyclopentyl)-Cis-5-Heptenoic Acid and 7-(5β-Hydroxy-2β-[(5R)-3-Hydroxy-Trans-1-Octenyl]-1α-Cyclopentyl)-Cis-5-Heptenoic Acid An ice-cooled solution of 4.0 g. of 7-(2β-[(3R)-3-hydroxy-trans-1-ocetenyl]-5-oxo-1α-cyclopent-3-enyl)-cis-5-heptenoic acid in 110 ml. of a 10:1 mixture methanol water is treated with 2.2 g. of sodium borohydride, and stirred at 25° for 7 hours. The mixture is concentrated under vacuum at 40°, the residue diluted with water, acidified with acetic acid and the mixture partitioned with ether. After washing and drying, the extract is evaporated and the residue chromatographed on silica. Elution with 35% ethyl acetate-hexane affords the first title product as an oil, $\lambda_{max}^{film}$ 2.95, 3.4, 5.8, 7.1, 8.1, 8.8, 9.7, 10.3 μ NMR: δ 5.48 (M, 4, olefinic H), 4.62 (2, OH), 4.28 (M, 2, 9 and 15-H) ppm. Mass spectrum: M+ at m/e (theory 338), M+-H$_2$O at m/e 320.2331 (theory 320.2350).

Further elution with 40% ethyl acetate-hexane gives the second title product as an oil, $\lambda_{max}^{film}$ 3.0, 3.4, 5.8, 7.1, 8.1, 9.35, 10.3 μ NMR: δ 5.55 (M, 4, olefinic H), 4.58 (s, OH), 4.05 (M, 2, 9 and 15-H) ppm. Mass spectrum: M+ at m/e 338 (theory 338). M+-H$_2$O at m/e 320.2384 (theory 320.2350).

EXAMPLE 2

7-[5α-Hydroxy-2β-(3-Oxo-Trans-1-Octentyl)-1α-Cyclopentyl]-Cis-5-Heptenoic Acid

A solution of 3.63 g. of 7-(5α-hydroxy-2β-[(3R-3-hydroxy-trans-1-octenyl]-1α-cyclopentyl)-cis-5-heptenoic acid in 250 ml. of dioxane is treated with 3.63 g. of 2,3-dichloro-5,6-dicyano-1,4-benzoquinone and stirred at 55° for 40 hours under nitrogen. The solution is concentrated under vacuum at 40° and the residue chromatographed on silica. Elution with 30% ethyl acetate-hexane yields 1.8 g. of the title product as an oil, $\lambda_{max}^{film}$ 3.0 (shoulder), 3.4, 5.8, 6.0 (shoulder), 6.15 (shoulder), 7.1, 8.1, 10.2 μ UV: $\lambda_{max}^{EtOH}$ 232 mμ (ε 12,000). NMR: δ 6.72 (dd, 1, J=5.3 and 15, 13-H, 6.08 (d, 1, J=15, 14-H), 5.40 (M,2,5 and 6-H), 4.25 (M, 1, 9-H) ppm. Mass spectrum: QM+ at m/e 337 (theory 337), QM+-H$_2$O at m/e 319 (theory 319).

EXAMPLE 3

7-(5α-Hydroxy-2β-[(3RS)-3-Hydroxy-3-Methyl-Trans-1-Octenyl]-1α-Cyclopentyl)-Cis-5-Heptenoic Acid An ice-cooled solution of 1.7 g. of 7-[5α-hydroxy-2β-(3-oxo-trans-1-octenyl)-1α-cyclopentyl]-cis-5-heptenoic acid in 150 ml. of tetrahydrofuran is treated with 15 ml. of 3M methyl magnesium bromide in ether dropwise over 10 minutes, under nitrogen. After stirring at 0° for 45 minutes, the mixture is added to ammonium chloride solution, acidifed with acetic acid and extracted with ether. After washing and drying, the extract is evaporated and the residue chromatograhed on silica. Elution with 35% ethyl acetate-hexane affords 1.07 g. of the title product as an oil, $\lambda_{max}^{film}$ 3.0, 3.4, 5.8, 8.1, 10.3 μ NMR: δ 5.42 (M, 4, olefinic H), 5.12 (s, 3, OH), 4.20 (M, 1, 9-H), 1.28 (s, 15-CH$_3$) ppm. Mass spectrum: QM+-H$_2$O at m/e 335 (theory 335).

EXAMPLE 4

7-(2β-[(3RS)-3-Hydroxy-3-Methyl-Trans-1-Octenyl]-5-Oxo-1α-Cyclopentyl)-Cis-5-Heptenoic Acid An ice-cooled solution of 1.02 g. of 7-(5α-hydroxy-2β-[(3RS)-3-hydroxy-3-methyl-trans-1-octenyl]-1α-cyclopentyl)-cis-5-heptenoic acid in 80 ml. of acetone is treated dropwise with Jones reagent until the orange color persists. After stirring at 0° for ½ hour, the mixture is treated with 5 ml. of methanol and dilute sodium bicarbonate until basic. The mixture is diluted with water, acidified with acetic acid and extracted with ether. After washing and drying, the extract is evaporated and the residue chromatographed on silica. Elution with 30% ethyl acetate-hexane gives 0.12 g. of the title product as an oil, $\lambda_{max}^{film}$ 3.0, 3.4, 5.75, 7.1, 8.15, 8.65, 10.3 μ MNR: δ 6.80 (s, 2, OH), 5.72 (M, 2, 13 and 14-H), 5.52 (M, 2, 5 and 6-H), 1.30 (s, 15-CH$_3$) ppm. Mass spectrum: QM+ at m/e 351 (theory 351).

EXAMPLE 5

5α-Hydroxy-2β-[(3RS)- - Hydroxy-3-Methyl-Trans-1-Octenyl]-1α-Cyclopentane Heptanoic Acid A solution of 2.5 g of 7-(5α-hydroxy-2β-[(3RS)-3-hydroxy-3-methyl-trans-1-octenyl]-1α-cyclopentyl)-cis-5-heptenoic acid in 35 ml. of 1:1 benzene-ethanol is added to a prehydrogenated solution of 0.63 g of tris-(triphenylphosphine) rhodium (I) chloride in 115 ml. of 1:1 benzene-ethanol and the mixture hydrogenated at 25° and atmospheric pressure until 1 equivalent of hydrogen is absorbed. Evaporation of the solvent and silica chromatography of the residue with 45% ethyl acetate-hexane gives 1.878 g. of the title product as an oil, $\lambda_{max}^{film}$ 3.0, 3.5, 5.85, 6.85, 8.95, 10.3 μ. NMR: δ 5.55 (M,2, 13 and 14-H), 4.98 (s, 3, OH), 4.32 (M, 1, 9-H) ppm. Mass spectrum: QM+-2H$_2$O at m/e 319.2636 (theory 319.2636).

EXAMPLE 6

2β-[(3RS)-3-Hydroxy-3-Methyl-Trans-1-Octenyl]-5-Oxo-1α-Cyclopentaneheptanoic Acid An ice-cooled solution of 1.795 g. of 5α-hydroxy-2β-[(3RS)-3-hydroxy-3-methyl-trans-1-octenyl]-1α-cyclopentaneheptanoic acid in 120 ml. of acetone is treated dropwise with Jones reagent until the orange color persists. After stirring at 0° for 25 minutes, the mixture is treated with 10 ml. of methanol and dilute sodium bicarbonate until basic. Following dilution with water, the mixture is acidified with acetic acid and extracted with ether. The extract is washed, dried, evaporated and the residue chromatographed on silica. Elution with 30% ethyl acetate-hexane affords 0.33 g. of the title product as an oil, $\lambda_{max}^{film}$ 2.95 (shoulder), 3.4, 5.75, 6.8, 8.6, 10.25 μ. NMR: δ 6.22 (OH), 5.62 (M, 13 and 14-H), 1.28, 1.28 (15-CH$_3$) ppm. Mass spectrum: QM+-H$_2$O at m/e 335 (theory 335).

EXAMPLE 7

2β-[(3RS)-3-Hydroxy-3-Methyloctyl]-5-Oxo-1α-Cyclopentaneheptanoic Acid

A solution of 0.29 g. of 2β-[(3RS)-3-hydroxy-3-methyl-trans-octenyl]-5-oxo-1α-cyclopentaneheptanoic acid in 20 ml. of ethyl acetate is added to a prehydrogenated mixture of 0.09 g. of 10% Pd/C in 10 ml. of ethyl acetate and the mixture hydrogenated at 25% and atmospheric pressure for 16 hours. The mixture is filtered, evaporated and the residue chromatographed on silica. Elution with 40% ethyl acetate-hexane gives 0.16 g. of the title product as an oil, $\lambda_{max}^{film}$ 3.0, 3.4, 5.72, 6.8, 8.65 μ NMR: 6.02 (s, OH), 1.18 (s, 15-CH$_3$) ppm. Mass spectrum: M+ at m/e 354.2729 (theory 354.2768).

EXAMPLE 8

5β-Hydroxy-2β-[(3R)-3-Hydroxy-Trans-1-Octenyl]-1α-Cyclopentaneheptanoic Acid

A solution of 4.4 g. of 7-(5β-hydroxy-2β-[(3R)-3-hydroxy-trans-1-octenyl]-1α-cyclopentyl)-cis-5-heptenoic acid in 50 ml. of 1:1 benzene-ethanol is added to a prehydrogenated solution of 1.1 g. of tris-(tripenylphosphine) rhodium (I) chloride in 200 ml. of 1:1 benzene-ethanol and the mixture hydrogenated at 25° and atmospheric pressure until 1 equivalent of hydrogen is absorbed. Evaporation of the solvents and silica chromatography of the residue with 40% ethyl acetate-hexane affords 2.7 g. of the title product as an oil, $\lambda_{max}^{film}$ 3.05, 3.4, 5.85, 6.8, 8.1, 9.8, 10.3 μ. NMR: δ 5.58 (M, 2, 13 and 14-H), 3.95 (M,2,9 and 15-H) ppm. Mass spectrum: M+ at m/e 340 (theory 340), M+-H$_2$0 at m/e 322.2493 (theory 322.2507).

EXAMPLE 9

5β-Hydroxy-2β-(3-Oxo-Trans-1-Octenyl)-1α-Cyclopentane Heptanoic Acid

A solution of 2.7 g. of 5β-hydroxy-2β-[(3R)-3-hydroxy-trans-1-octenyl]-1α-cyclopentane heptanoic acid in 150 ml. of dioxane is treated with 2.7 g. of 2,3-dichloro-5,6-dicyano-1,4-benzoquinone and the mixture stirred at 75° for 18 hours under nitrogen. After cooling to 25°, the mixture is filtered, diluted with ether, filtered again and washed with water. The ether solution is then extracted 4 times with aqueous saturated sodium bicarbonate and the aqueous extracts acidified with acetic acid and extracted with ether. The ether extract is combined with the original ether solution, evaporated and the residue chromatographed on silica. Elution with 40% ethyl acetate-hexane gives 1.42 g. of the title product as an oil, $\lambda_{max}^{film}$ 3.0 (shoulder), 3.4, 5.85, 6.0 (shoulder), 6.15, 8.4, 9.35, 10.2 μ. UV: $\lambda_{max}^{EtOH}$ 230 mμ (ε 13,200). NMR: δ 6.8 (dd, 1, J=7.5 and 15, 13-H), 6.0 (d, 1, J=15, 14-H), 3.95 (M, 1, 9-H) ppm. Mass spectrum: QM+ at m/e 339 (theory 339).

EXAMPLE 10

2β-[(3RS)-3-Ethynyl-3-Hydroxy-Trans-1-Octenyl]-5β-Hydroxy-1α-Cyclopentane Heptanoic Acid A solution of 1.421 g. of 5β-hydroxy-2β-(3-oxo-trans-1-octenyl)-1α-cyclopentane heptanoic acid in 30 ml. of tetrahydrofuran is added to an ice-cooled solution of ethynyl magnesium bromide (made from 13.3 ml. of 3M methyl magnesium bromide and excess acetylene) in 170 ml. of tetrahydrofuran and the mixture stirred at 0° for 15 minutes and at 25° for 3 hours. The mixture is diluted with aqueous ammonium chloride solution, acidified with acetic acid and extracted with ether. After washing and drying, the extract is evaporated and the residue chromatographed on silica. Elution with 40% ethyl acetate-hexane affords 1.03 g. of the title product as an oil, $\lambda_{max}^{film}$ 3.05, 3.4, 5.8, 9.3, 10.3 μ. NMR: δ 5.95 (dd, 1, J=7.5 and 15, 13-H), 5.4 (d, 1, J=15, 14-H), 3.92 (M, 1, 9-H, 2.58 (s, 1, acetylenic H) ppm. Mass spectrum: QM+ at m/e 365 (theory 365).

EXAMPLE 11

2β-[(3RS)-3-Ethynyl-3-Hydroxy-Trans-1-Octenyl]-5-Oxo-1α-Cyclopentane Heptanoic Acid An ice-cooled solution of 1.0 g. of 2β-[(3RS)-3-ethynyl-3-hydroxy-trans-1-octenyl]-5β-hydroxy-1α-cyclopentaneheptanoic acid in 75 ml. of acetone is treated with Jones reagent (3.9 ml.) over 20 minutes until the orange color persists. After stirring at 0° for ½ hour, under nitrogen, the mixture is treated with 10 ml. of methanol and dilute sodium bicarbonate until basic. Following dilution with water and acidification with acetic acid, the mixture is extracted with ether and the extract wadhed, dried and evaporated. Silica chromatography of the residue with 30% ethyl acetatehexane gives 0.27 g. of the title product as an oil, $\lambda_{max}^{film}$ 3.05, 3.45, 5.8, 7.1, 8.65, 10.3 μ. NMR: δ 5.98 (dd, 1, J=7.5 and 15, 13-H), 5.55 (d, 1, J=13, 14-H), 2.60 (s, 1, acetylenic H) ppm. Mass spectrum: QM+ at m/e 363 (theory 363).

EXAMPLE 12

7-[5β-Hydroxy-2β-(3-Oxo-Trans-1-Octenyl)-1α-Cyclopentyl]-Cis-5-Heptenoic Acid A solution of 0.51 g. of 7-(5β-hydroxy-2β-[(3R)-3-hydroxy-trans-1-octenyl]-1α-cyclopentyl)-cis-5-heptenoic acid in 40 ml. of dioxane is treated with 0.51 g. of 2,3-dichloro-5,6-dicyano-1,4-benzoquinone and the mixture stirred at 55° for 24 hours under nitrogen. The mixture is evaporated and the residue chromatographed on silica with 40% ethyl acetate-hexane to obtain 0.38 g. of the title product as an oil, $\lambda_{max}^{film}$ 3.0 (shoulder), 3.4, 5.85, 6.0 (shoulder), 6.15 (shoulder), 8.1, 9.3, 10.2 μ. UV: $\lambda_{max}^{EtOH}$ 231 mμ (ε 14,050). NMR: δ 6.85 (dd, 1, J=7.5 and 16, 13-H), 6.08 (d, 1, J=16, 14-H), 5.50 (M, 2, 5 and 6-H), 4.00 (M, 1, 9-H) ppm. Mass apectrum: M+ at m/3.336.2299 (theory 336.2299).

EXAMPLE 13

5β-Hydroxy-2β-(3Oxo-Octyl)-1α-Cyclopentaneheptanoic Acid

A solution of 2.68 g. of 7-[5β-hydroxy-2β-(3-oxo-trans-1-octenyl)-1α-cyclopentyl]-cis-5-heptenoic acid in 50 ml. of ethyl acetate is added to a prehydrogenated mixture of 0.67 g. of 10% Pd/C in 50 ml. of ethyl acetate and hydrogenated at 25° and atmospheric pressure until 2 equivalents of hydrogen are absorbed. The mixture is filtered, evaporated and the residue chromatographed on silica. Elution with 35% ethyl acetate-hexane affords 1.96 g. of the title product as an oil, $\lambda_{max}^{film}$ 3.0 (shoulder), 3.4, 5.8, 6.8, 7.05, 8.2 μ. NMR: δ 6.35 (s, 2, OH), 3.95 (m, 1, 9-H), 2.2–2.6 (M, 5, CO-CH) ppm. Mass spectrum: QM+-H₂O at m/e 323 (theory 323).

EXAMPLE 14

2β-[(3RS)-3-Ethynyl-3-Hydroxyoctyl]-5β-Hydroxy-1α-Cyclopentaneheptanoic Acid A solution of 1.86 g. of 5β-hydroxy-2β-(3-oxo-octyl)-1α-cyclopentane heptanoic acid in 30 ml. of tetrahydrofuran is added to a solution of ethynyl magnesium bromide (made from 18.0 ml. of 3M methyl magnesium bromide in ether and excess acetylene) in 220 ml. of tetrahydrofuran and the mixture stirred at 25° for 2 hours under nitrogen. Following dilution with aqueous ammonium chloride solution and acidification with acetic acid, the mixture is extracted with ether. After washing and drying, the extract is evaporated and the residue chromatographed on silica. Elution with 40% ethyl acetate-hexane gives 1.54 g. of the title product as an oil, $\lambda_{max}^{film}$ 3.05, 4.5, 5.8, 6.8, 9.0, 10.7 μ. NMR: δ 5.32 (s, 3, OH), 3.95 (M, 1, 9-H), 2.48 (s, 1, acetylenic H), 2.35 (M, 2, CO-CH) ppm. Mass spectrum: QM+-2H₂O at m/e 331.2633 (theory 331.2336).

EXAMPLE 15

2β-[(3RS)-3-Ethynyl-3-Hydroxyoctyl]-5-Oxo-1α-Cyclopentane Heptanoic Acid

An ice-cooled solution of 1.45 g. of 2β-[(3RS)-3-ethynyl-3-hydroxyoctyl]-5β-hydroxy-1α-cyclopentaneheptanoic acid in 50 ml. of acetone is treated with Jones reagent (4.0 ml.) until the orange color persisted and the mixture stirred at 0° for ¼ hour under nitrogen. The mixture is treated with 10 ml. of methanol, dilute sodium bicarbonate until basic and diluted with water. After acidification with acetic acid, the mixture is extracted with ether and the extract washed, dried and evaporated. Silica chromatography of the residue with 30% ethyl acetatehexane gives 0.32 g. of the title product as an oil, $\lambda_{max}^{film}$ 3.05, 3.4, 4.7 (weak), 5.75, 6.8, 7.05, 8.6 μ. NMR: δ 6.02 (M, OH), 2.48 (s, acetylenic H) ppm. Mass spectrum: QM+-H₂O at m/e 347 (theory 347).

EXAMPLE 16

7-(2β-[(3RS)-3-Ethynyl-3-Hydroxy-Trans-1-Octenyl]-5β-Hydroxy-1α-Cyclopentyl)-Cis-5-Heptenoic Acid A solution of 9.95 g. of 7-[5β-hydroxy-2β-(3-oxo-trans-1-octenyl)-1α-cyclopentyl]-cis-5-heptenoic acid in 20 ml. of tetrahydrofuran is added to a solution of ethynyl magnesium bromide (made from 18.9 ml. of 3M methyl magnesium bromide and excess acetylene) in 270 ml. of tetrahydrofuran and the mixture stirred at 25° for 1 hour under nitrogen. The mixture is diluted with aqueous ammonium chloride solution, acidified with acetic acid and extracted with ether. Following washing and drying, the extract is evaporated and the residue chromatographed on silica. Elution with 35% ethyl acetate-hexane affords 1.55 g. of the title product as an oil, $\lambda_{max}^{film}$ 3.05, 3.4, 5.8, 10.25 μ. NMR: δ 6.00 (dd, 1, J=7.5 and 15, 13-H), 5.52 (M, 2, 5 and 6-H), 5.48 (d, J=15, 14-H), 4.00 (M, 1, 9-H), 2.58 (s, 1, acetylenic H) ppm.

EXAMPLE 17

7-(2β-[(3R)-3-Ethynyl-3-Hydroxy-Trans-1-Octenyl]-5-Oxo-1α-Cyclopentyl)-Cis-5-Heptenoic Acid and

7-(2β-[(3S)-3-Ethynyl-3-Hydroxy-Trans-1-Octenyl]-5-Oxo-1α-Cyclopentyl)-Cis-5-Heptenoic Acid An ice-cooled solution of 1.415 g. of 7-(2β-[(3RS)-3-ethynyl-3-hydroxy-trans-1-octenyl]-5β-hydroxy-1α-cyclopentyl-cis-5-heptenoic acid in 80 ml. of acetone is treated with Jones reagent until the orange color persists and the mixture stirred at 0° for ¼ hour under nitrogen. The mixture is treated with 10 ml. of methanol, dilute sodium bicarbonate until basic and diluted with water. Following acidification with acetic acid, the mixture is extracted with ether and the extract washed, dried and evaporated. The resulting residue is chromatographed on silica with 30% ethyl acetate-hexane to obtain 0.11 g. of a first product as an oil, $\lambda_{max}^{film}$ 3.05, 3.4, 5.75, 7.05, 8.1, 8.6, 10.25 μ. NMR: δ 7.22 (s, 2, OH), 5.3–6.4 (M, 4 olefinic H), 2.60 (s, acetylenic H) ppm. Mass spectrum: M+ at m/e 360 (theory 360), M+-C₂H₂ at m/e 334.2143 (theory 334.2193).

Continued elution afforded 0.04 g. of a second product, as an oil, which exhibits spectra identical to that of the first product. On the basis of relative mobility in thin layer chromatography the second product is assigned the 3S configuration and the first product is assigned the 3R configuration.

EXAMPLE 18

Anesthetized (Dial-urethane) guinea pigs were artificially respired at a constant positive air pressure (Starling miniature pump) and changes in tidal air during inspiration were recorded, according to the method of Rosenthale et al., Int. Arch. Pharmacol., 172, 91 (1968). The bronchoconstrictor agent acetylcholine (ACH) was administered at doses of 10 to 40 meg/kg. depending on each animal's sensitivity to this compound, and control responses to acetylcholine were thus established. Bronchoconstrictor agents raise the resistance of the lungs to inflation thereby decreasing the tidal air flow. 7-(2$\beta$-[(3S)-3-ethynyl-3-hydroxy-trans-1-octenyl]-5-oxo-1$\alpha$-cyclopentyl)-cis-5-heptenoic acid was then administered be aerosol, and the animals were then challenged again with acetylcholine, and the degree of inhibition of bronchoconstriction was thus determined. A minimum of two animals was used at each dose.

| Total Aerosol Dose (mcg) | Results[a] Mean % Protection VS ACH Bronchoconstriction |
|---|---|
| $1.5 \times 10^{-4}$ | 32 |
| $10^{-3}$ | 53 |
| $10^{-2}$ | 79 |
| $10^{-1}$ | 92 |

[a]Minimum of 2 animals per dose.

EXAMPLE 19

7-[2$\beta$-(3-Oxo-Trans-1-Octenyl)-5-Oxo-1$\alpha$-Cyclopentyl]-Cis-5-Heptenoic Acid A solution of 20.0 g. of 15-epi-PGA$_2$ in 500 ml. of methanol and 50 ml. of water is cooled in an ice bath and treated with 11.0 g. of sodium borohydride in portions (some foaming) with stirring. After addition of sodium borohydride, the ice bath is removed and the mixture stirred at 25° for 6 hours. The mixture is acidified with acetic acid and the solvent removed under vacuum (water aspirator) at 40°. The residue is diluted with water and extracted thrice with ether. The extract is washed thrice with brine, dried and evaporated (aspirator/40°) to yield 22 g. of oil, a mixture of C-9 alcohols. TLC (silica, 65:15:2 Bz:Diox:HAc) shows starting ketone at Rf 45 and alcohol products at Rf 42 and 48.

The above crude alcohol mixture is dissolved in 1.5 liters of acetone, cooled in an ice bath and treated with 120 ml. of 1.4M Jones reagent. After stirring at 0° for 40 minutes, the mixture is treated with 50 ml. of methanol to destroy excess Jones reagent, neutralized with dilute sodium bicarbonate solution and acidified with acetic acid. The solvent is removed (aspirator/40°) and the residue diluted with water and extracted thrice with ether. The extract is washed thrice with brine, dried and evaporated (aspirator/40°). The residue (24 g.) is chromatographed on 1.2 Kg of silicar CC-4 starting with 15% EtOAc-hexane and the oily title product (13.4 g.) is eluted with 30% EtOAc-hexane. TLC (silica 65:15:2 Bz:Diox:HAc) Rf 55. UV: $\lambda_{max}$ $^{95\% EtOH}$ 228 m$\mu$ ($\epsilon$ 13,000). $\lambda_{max}$$^{film}$ 3.45, 5.75, 5.9, 6.0, 6.15, 7.1, 8.7, 10.2 $\mu$. NMR: $\delta$ 10.7 (s, 1, OH), 6.86 (dd, 1, J=7.5 and 15, 13-H), 6.2 (d, 1, J=15, 14-H), 5.4 (m, 2, 5 and 6-H) ppm. Analysis for: C$_{20}$H$_{30}$O$_4$ Calculated: C, 71.82; H, 9.04 Found: C, 72.01; H, 9.00

EXAMPLE 20

7-(7$\beta$-[3-Oxo-Trans-1-Octenyl]-1,4-Dioxaspiro[4.4]non-6$\alpha$-yl)-Cis-5-Heptenoic Acid A solution of 4.8 g. of 7-[2$\beta$-(3-oxo-trans-1-octenyl)-5-oxo-1$\alpha$-cyclopentyl]-cis-5-heptenoic acid, 50 ml. of ethylene glycol and 80 mg. of p-toluenesulfonic acid is refluxed under nitrogen with a Dean Stark water separator for 1.5 hours. The mixture is cooled, diluted with 300 ml. of ether, washed thrice with brine and dried. The solvent is removed (aspirator/40°) and the residue (5.5 g.) chromatographed on 300 g. of silicar CC-4. The crude product is put on the column with 15% ethyl acetatehexane, allowed to stand for 4 hours and then eluted to obtain the oily title product (3.1 g.) with 20% EtAc-hexane. TLC (silica 65:15:2 Bz:Diox:HAc) shows starting diketone at Rf 50, desired C-9 monoketal at Rf 55 and C-9, 15 diketal at Rf 60. UV: $\lambda_{max}$$^{95\% EtOH}$ 230 m$\mu$ ($\epsilon$ 12,840). $\lambda_{max}$$^{film}$ 3.45, 5.75, 5.85, 6.0, 6.15, 8.7, 9.65, 10.2 $\mu$. NMR: $\delta$ 10.2 (s, 1, OH), 6.82 (dd, 1, J=7.5 and 16.5, 13-H), 6.1 (d, 1, J=16.5, 14-H), 5.42 (m, 2, 5 and 6-H), 3.92 (s, 4, ketal H) ppm. Mass spectrum: M+ at m/e 378.2423 (theory 378.2405).

EXAMPLE 21

7-(7$\beta$-[(3S)-3-Ethynyl-3-Hydroxy-Trans-1-Octenyl]-1,4-dioxaspiro[4.4]non-6$\alpha$-yl)-Cis-5-Heptenoic Acid Dry tetrahydrofuran is saturated at 25° by bubbling acetylene (through 2 dry ice-acetone traps and alumina drying tube) through with stirring for approximately $\frac{1}{2}$ hour. A solution of 50 ml. of 3M methyl magnesium bromide/ether in 50 ml. of dry tetrahydrofuran is added dropwise and stirring continued for 1 hour with acetylene continuously bubbling through the mixture. A solution of 9.0 g. of 7-(7$\beta$-[3-oxo-trans-1-octenyl]-1,4-dioxaspiro[4.4]non-6$\alpha$-yl)-cis-5-heptenoic acid in 120 ml. of dry tetrahydrofuran is added and the mixture stirred for 1 hour with acetylene continuously bubbling through the mixture. The mixture is added to ammonium chloride solution, acidified with acetic acid, and extracted thrice with ether. The extract is washed thrice with brine, dried and evaporated (aspirator/40°). Chromotography of the residue (11 g.) on 1 Kg of silicar CC-4 with 25% ethyl acetate-hexane first gives 3.9 g. of the 15-epi isomer followed by 5.2 g. of the desired oily title product. TLC (silica 65:15:2 Bz:Diox:HAc) shows starting ketal at Rf 55, title product at Rf 48. $\lambda_{max}$$^{film}$ 3.0, 5.4, 4.7 (weak), 5.75, 8.6, 10.2 $\mu$. NMR: $\delta$ 5.3–6.1 (m, 4, olefinic), 5.9 (s, 4 ketal H), 2.58 (s, C$\equiv$CH)ppm. Mass spectrum: M+ at m/3.404.2561 (theory 404.2558).

EXAMPLE 22

7-(2$\beta$-[(3S)-3-Ethynyl-3-Hydroxy-Trans-1-Octenyl]-5-Oxo-1$\alpha$-Cyclopentyl)-Cis-5-Heptenoic Acid A solution of 5.2 g. of 7-(7$\beta$-[(3S)-3-ethynyl-3-hydroxy-trans-1-octenyl]-1,4-dioxaspiro[4.4]non-6$\alpha$-yl)-cis-5-heptenoic acid in 150 ml. of acetic acid is treated with 75 ml. of water and stirred at 25°/N$_2$/1 hour. The solution is diluted with brine, extracted thrice with ether and the extract washed 5 times with brine, dried and evaporated (aspirator/40°). The crude product (5.4 g.) is chromatographed on 520 g. silicar CC-4 and the title product (3.9 g. of oil) eluted with 30% EtOAc-hexane. $[\alpha]_D^{25°}(-) 58.5$ (1% CHCl$_3$). $\lambda_{max}$$^{film}$ 3.0, 3.35, 5.7, 7.0, 8.55, 10.2$\mu$. NMR: $\delta$ 6.1 (dd, 1, J=7.5 and 15, 13-H), 5.65 (d, 1, J=15, 14-H) 5.48 (m, 2,5 and 6-H), 2.65 (s, C$\equiv$CH)ppm. Mass spectrum: M+ at m/e 360.

The subject matter which the applicant regards as his invention is particularly pointed out and claimed as follows:

1. A process for relieving bronchial spasm and facilitating breathing in warm-blooded animals which comprises administering to a warm-blooded animal in need thereof an amount sufficient to relieve bronchial spasm and facilitate breathing in said warm-blooded animal of a prostanoic acid of the formula:

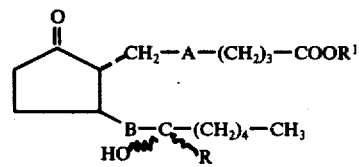

wherein R is ethynyl, A is —CH$_2$—CH$_2$— and B is —CH$_2$—CH$_2$—; R is ethynyl, A is —CH$_2$—CH$_2$—, and B is trans —CH=CH—; or R is ethynyl, A is cis —CH=CH—; and B is trans —CH=CH—; and R$^1$ is hydrogen, alkyl of from 1 to about 6 carbon atoms, alkali metal, or a pharmacologically acceptable cation derived from ammonia or a basic amine.

2. A process according to claim 1 wherein R is ethynyl, A is cis —CH=CH—, and B is trans —CH=CH—.

* * * * *